(12) United States Patent
Mistretta et al.

(10) Patent No.: US 10,134,144 B2
(45) Date of Patent: Nov. 20, 2018

(54) SYSTEM AND METHOD FOR DETERMINING DYNAMIC PHYSIOLOGICAL INFORMATION FROM FOUR-DIMENSIONAL ANGIOGRAPHIC DATA

(71) Applicant: Wisconsin Alumni Research Foundation, Madison, WI (US)

(72) Inventors: Charles A. Mistretta, Madison, WI (US); Charles M. Strother, Madison, WI (US); Gabriel Shaughnessy, Nashotah, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 57 days.

(21) Appl. No.: 14/855,209

(22) Filed: Sep. 15, 2015

(65) Prior Publication Data
US 2017/0076467 A1 Mar. 16, 2017

(51) Int. Cl.
*A61B 5/02* (2006.01)
*G06T 7/20* (2017.01)
*G06T 7/00* (2017.01)

(52) U.S. Cl.
CPC .............. *G06T 7/2053* (2013.01); *A61B 5/02* (2013.01); *G06T 7/0081* (2013.01); *G06T 7/206* (2013.01);
(Continued)

(58) Field of Classification Search
CPC ....... A61B 3/1233; A61B 3/1241; A61B 5/02; A61B 5/02007; A61B 5/02035;
(Continued)

(56) References Cited

U.S. PATENT DOCUMENTS 5,438,992 A 8/1995 Siegel, Jr. et al.
6,169,917 B1 * 1/2001 Masotti ............... A61B 6/4441
600/407

(Continued)

OTHER PUBLICATIONS

Hoffmann, et al., Determination of Instantaneous and Average Blood Flow Rates from Digital Angiograms of Vessel Phantoms Using Distance-Density Curves, Invest. Radial., 1991, 26:207-212.
(Continued)

*Primary Examiner* — Carol Wang
(74) *Attorney, Agent, or Firm* — Quarles & Brady LLP

(57) ABSTRACT

A system and method are provided for generating time resolved series of angiographic volume data having flow information. The system and method are configured to receive angiographic volume data acquired from a subject having received a dose of a contrast agent using an imaging system and process the angiographic volume data to generate angiographic volume images. The angiographic volume data is processed to derive flow information by determining a distance between two points along a vessel in the angiographic volume images and determining a phase at each of the two points along the vessel in the angiographic volume images. A flow direction or a velocity of flow within the vessel is determined using the distance between the two points along the vessel and the phase at each of the two points along the vessel.

15 Claims, 13 Drawing Sheets

(52) U.S. Cl.
CPC .............. *G06T 2207/10076* (2013.01); *G06T 2207/10116* (2013.01); *G06T 2207/20224* (2013.01); *G06T 2207/30104* (2013.01); *G06T 2210/41* (2013.01)

(58) Field of Classification Search
CPC ......... A61B 5/026; A61B 5/029; A61B 6/504; A61B 8/06; A61B 8/065; A61B 8/0891; G06T 2207/30004; G06T 2207/30104; G06T 2207/30101; G06T 2211/404
See application file for complete search history.

(56) References Cited

U.S. PATENT DOCUMENTS

| | | | |
|---|---|---|---|
| 6,176,832 B1* | 1/2001 | Habu | A61B 5/0285 600/485 |
| 6,520,913 B1 | 2/2003 | Pesavento et al. | |
| 8,643,642 B2 | 2/2014 | Mistretta et al. | |
| 2003/0149366 A1* | 8/2003 | Stringer | A61B 8/0833 600/464 |
| 2006/0235669 A1 | 10/2006 | Charbel et al. | |
| 2008/0077010 A1 | 3/2008 | Cohen-Solal et al. | |
| 2008/0269611 A1 | 10/2008 | Pedrizzetti et al. | |
| 2011/0037761 A1* | 2/2011 | Mistretta | A61B 6/4441 345/419 |
| 2013/0046176 A1 | 2/2013 | Mistretta et al. | |
| 2013/0096419 A1* | 4/2013 | Miyazaki | G01R 33/56308 600/419 |
| 2013/0345559 A1* | 12/2013 | Haemmerich | A61B 5/0275 600/431 |
| 2014/0313196 A1 | 10/2014 | Mistretta et al. | |
| 2015/0313466 A1* | 11/2015 | Yoshida | A61B 5/0066 600/425 |
| 2016/0267704 A1 | 9/2016 | Mistretta et al. | |

OTHER PUBLICATIONS

Lieber, et al., Functional Angiography, Critical Reviews in Biomedical Engineering, 2005, 33(1):1-102.

Lieber, et al., The Mixability of Angiographic Contrast with Arterial Blood, Med. Phys., 2009, 36(11):5064-5078.

Shpilfoygel, et al., X-ray Videodensitometric Methods for Blood Flow and Velocity Measurement: A Critical Review of Literature, Med. Phys, 2000, 27(9):2008-2023.

PCT International Search Report and Written Opinion, PCT/US2016/051453, dated Jan. 10, 2017.

* cited by examiner 700 f=0.05, Δt=0
702 f=0.05, Δt=2

— f=0.05, Δt=0 vs t=2

704 f=0.05, Δt=0
706 f=0.05, Δt=2

— f=0.05, Δt=0 vs t=2

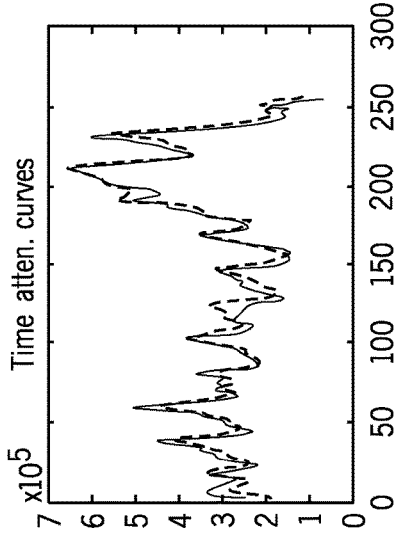
FIG. 8E
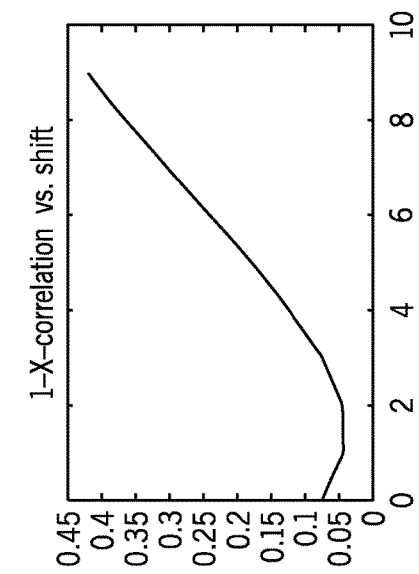
FIG. 8F
FIG. 8G
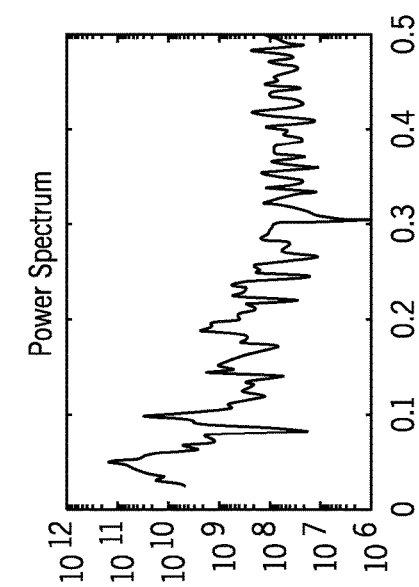
FIG. 8H

SYSTEM AND METHOD FOR DETERMINING DYNAMIC PHYSIOLOGICAL INFORMATION FROM FOUR-DIMENSIONAL ANGIOGRAPHIC DATA

STATEMENT REGARDING FEDERALLY SPONSORED RESEARCH

This invention was made with government support under HL116567 awarded by the National Institutes of Health. The government has certain rights in the invention.

CROSS-REFERENCE TO RELATED APPLICATIONS

N/A

BACKGROUND

The present disclosure is directed to x-ray angiography and, in particular, the disclosure relates to a system and method for determining dynamic information from time-resolved, three-dimensional (3D) angiographic images, referred to as four-dimensional (4D) angiographic x-ray data.

Since the introduction of angiography beginning with the direct carotid artery punctures of Moniz in 1927, there have been ongoing attempts to develop angiographic techniques that provide diagnostic images of the vasculature, while simultaneously reducing the invasiveness associated with the procedure. In the late 1970's, a technique known as digital subtraction angiography (DSA) was developed based on real-time digital processing equipment. Due to steady advancements in both hardware and software, DSA can now provide depictions of the vasculature in both 2D and volumetric 3D formats. Three-dimensional digital subtraction angiography (3D-DSA) has become an important component in the diagnosis and management of people with a large variety of central nervous system vascular diseases as well as other vascular diseases throughout the body.

In recent years competition for traditional DSA has emerged in the form of computed tomography angiography (CTA) and magnetic resonance angiography (MRA). CTA is a less invasive technique but has lower spatial resolution. It is is not time-resolved unless the imaging volume is severely limited. The images are not isotropic and secondary reconstruction yields degraded spatial resolution. CTA is also somewhat limited as a standalone diagnostic modality by artifacts caused by bone at the skull base and as well as the contamination of arterial images with opacified venous structures. Further, CTA provides no functionality for guiding or monitoring minimally-invasive endovascular interventions.

Significant advances have been made in both the spatial and the temporal resolution qualities of MRA. Currently, gadolinium-enhanced time-resolved MRA (TRICKS) is widely viewed as a dominant clinical standard for time-resolved MRA. TRICKS enables voxel sizes of about 10 mm$^3$ and a temporal resolution of approximately 10 seconds. Advancements such as HYBRID highly constrained projection reconstruction (HYPR) MRA techniques, which violate the Nyquist theorem by factors approaching 1000, can provide images with sub-millimeter isotropic resolution at frame times just under 1 second. Nonetheless, the spatial and temporal resolution of MRA are not adequate for all imaging situations and its costs are considerable. Furthermore, the spatial and temporal resolution is substantially below other methods, such as DSA.

The recently-introduced, four-dimensional (4D) DSA techniques can use rotational DSA C-arm imaging systems controlled with respect to a particular injection timing so that there is time dependence in the acquired reconstructed 4D volumes. As described in U.S. Pat. No. 8,643,642, which is incorporated herein by reference, a 3D DSA volume can be used as a constraining volume to generate a new 3D volume that contains the temporal information of each projection. As in 3D DSA, a mask rotation without contrast is followed by a second rotation during which contrast is injected. The process creates a series of time resolved 3D angiographic volumes that can be updated, for example, every $\frac{1}{30}$ of a second.

Thus, the above-described systems and methods have improved over time and, thereby, provided clinicians with an improving ability to visualize the anatomy of the vessels being studied. Of course, blood flow through vessels is dynamic and ideally both the dynamics of blood flow and the structural features of the vessels could be used by a clinician to deduce whether or not there was an abnormality. Currently, with ever increasing spatial and temporal resolution, the clinician has been provided with clearer and more accurate information about the geometry (i.e., anatomy) of the vessels. Unfortunately, assessment of the equally important dynamics of blood flow through the vasculature still depends upon a qualitative assessment gained from visualization of a contrast bolus as it passes through the vessels. As such, while the deductions made by the clinician about the structural dynamics and function of the vessel (i.e. anatomy) have correspondingly improved, even the best deductions about the circulatory dynamics (e.g. blood flow and velocity) are still qualitative and thus inherently limited.

Therefore, it would be desirable to a clinician performing an angiographic study to have a system and method for providing information about the functional or dynamic performance of the circulation as well as the vascular anatomy.

SUMMARY

The present disclosure overcomes the aforementioned drawbacks by providing a system and method for determining functional and/or dynamic flow information from 4D DSA, x-ray data. In particular, a system and method is provided that can determine dynamic information from a time-resolved angiographic study, including 4D DSA studies that provide time-resolved, anatomical angiographic images that include flow or velocity and velocity-derived information.

In accordance with one aspect of the disclosure, a system is disclosed for generating time resolved series of angiographic volume images having flow or velocity information integrated therewith. The system includes an image processing system configured to receive angiographic volume data acquired from a subject having received a dose of a contrast agent using an imaging system, process the angiographic volume data to generate angiographic volume images and process the angiographic volume data to derive flow information associated with vessels in the angiographic volume images. To do so, the image processing system determines a distance between two points along a vessel in the angiographic volume images, determines a phase at each of the two points along the vessel in the angiographic volume images, and determines at least one of a flow direction or a velocity of flow within the vessel using the distance between the two points along the vessel and the phase at each of the two points along the vessel. The system also includes a display configured to display the angiographic volume images of the subject and the at least one of the flow direction or the velocity of flow within the vessel.

In accordance with another aspect of the disclosure, a method is disclosed for generating time-resolved series of angiographic volume data having flow information integrated therewith. The method includes generating a series of 3D time-resolved vascular volumes from time resolved x-ray projection data, analyzing a signal indicating pulsatile flow through the vascular volumes in the series of 3D time-resolved vascular volumes to determine a temporal shift applied to a signal-versus-time curve at a first point in a selected vessel that matches a signal-versus-time curve at a second point in the selected vessel, and determining a distance between the first point and the second point in the selected vessel. The method also includes determining a velocity of flow between the first point and the second point in the selected vessel using the temporal shift and the distance between the first point and the second point in the selected vessel and displaying the 3D time-resolved vascular volumes with the velocity.

In accordance with yet another aspect of the disclosure, a system is disclosed for generating time resolved series of angiographic volume images having flow or velocity information integrated therewith. The system includes an image processing system configured to receive angiographic volume data acquired from a subject having received a dose of a contrast agent using an imaging system, process the angiographic volume data to generate angiographic volume images, and determine a distance between two points along a vessel in the angiographic volume images separated by a distance, $\Delta x$. The image processing system is further configured to analyze respective waveform of pulsatility for each of the two points along a vessel in the angiographic volume images and determine a point in a cross-correlation or sum-of-square differences between the respective waveform of pulsatility for each of the two points along a vessel to determine a time delay, $\Delta t$, corresponding to an estimate of the distance the blood has traveled during the time delay that agrees with the distance. The system also includes a display configured to provide the generate angiographic volume images correlated with the an indication of velocity between at least the two points along a vessel given by $\Delta x/\Delta t$.

In accordance with still another aspect of the disclosure, a system is provided for generating time resolved series of angiographic volume images having flow or velocity information integrated therewith. The system includes an image processing system configured to receive angiographic volume data acquired from a subject having received a dose of a contrast agent using an imaging system and process the angiographic volume data to generate angiographic volume images. The image processing system is further configured to process the angiographic volume data to derive flow information associated with vessels in the angiographic volume images by i) selecting one of two points along a vessel in the angiographic volume images or two time points within the angiographic volume images, ii) determining one of a phase at each of the two points along the vessel in the angiographic volume images or a spatial shift required to align the angiographic volume images from the two time points, iii) determining at least one of the phase or the spatial shift determined in ii). The system also includes a display configured to display the angiographic volume images of the subject and the at least one of the flow direction or the velocity of flow within the vessel.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
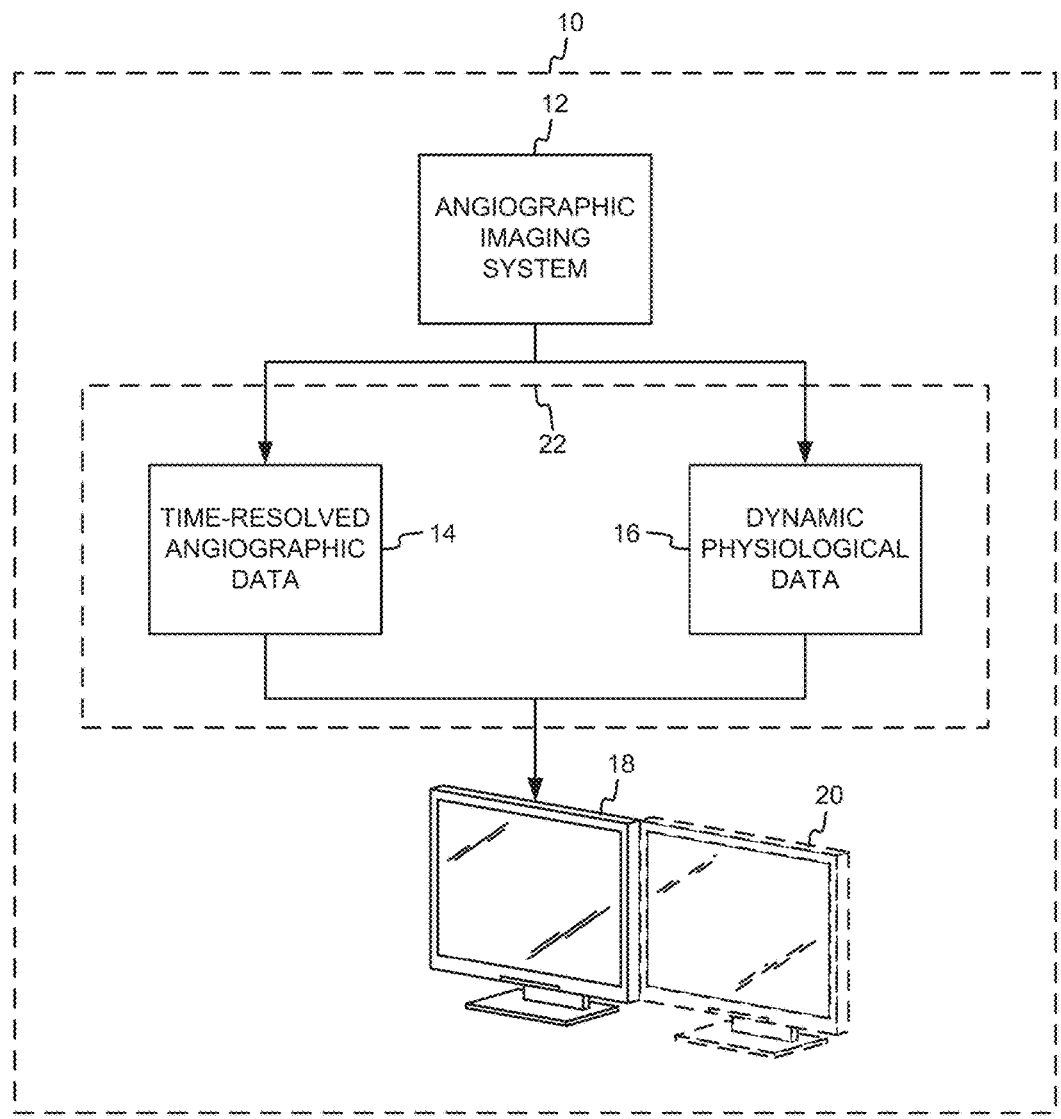
FIG. 1 is a block diagram of a system for creating time-resolved, three-dimensional (3D), angiographic images having dynamic physiological information in accordance with the present disclosure.

Referring to FIG. 1, a system 10 is illustrated for creating time-resolved angiographic images having dynamic physiological information, such as flow or velocity information. In particular, the system 10 includes an angiographic imaging system 12. As will be described, the angiographic imaging system 12 can be used to acquire time-resolved angiographic data 14, from which dynamic physiological information, such as flow or velocity data 16 can be derived. The time-resolved angiographic data 14 and flow or velocity data 16 can be processed and provided to a clinician via a display 18. As will be further described, the information may be provided to the clinician using multiple displays including a first display 18 and a secondary display 20 or multiple additional displays. As will also be described, the process of deriving dynamic physiological information, such velocity or flow data, can be performed partially or in whole using an image processing system, which may include a graphics processing unit (GPU) or other processor, including a central processing unit (CPU), 22.

Figure 2A:
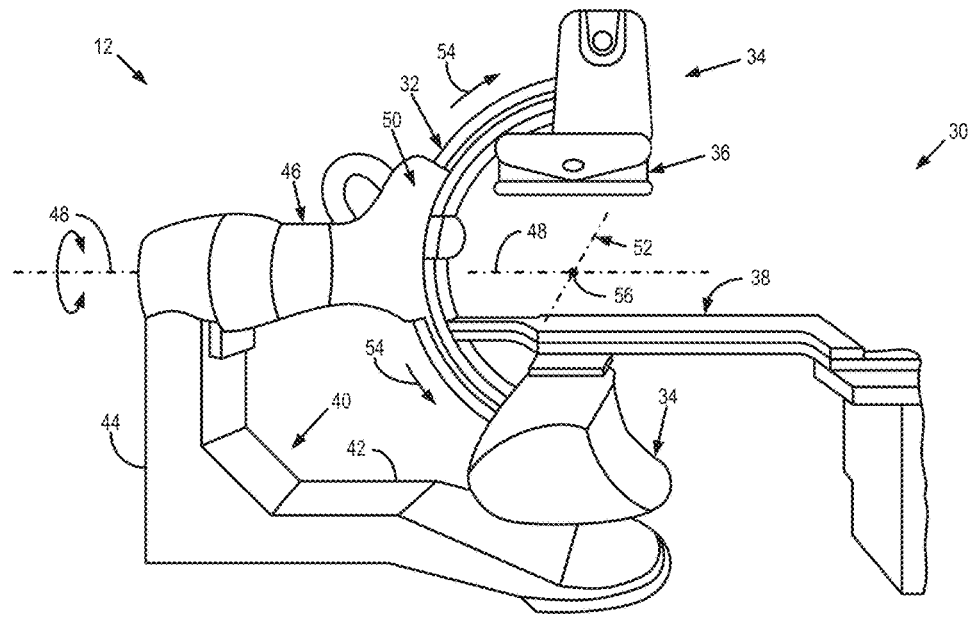
FIG. 2A is a perspective view of an example of an x-ray imaging system that can be used in accordance with the present disclosure to acquire angiographic data.
Figure 2B:
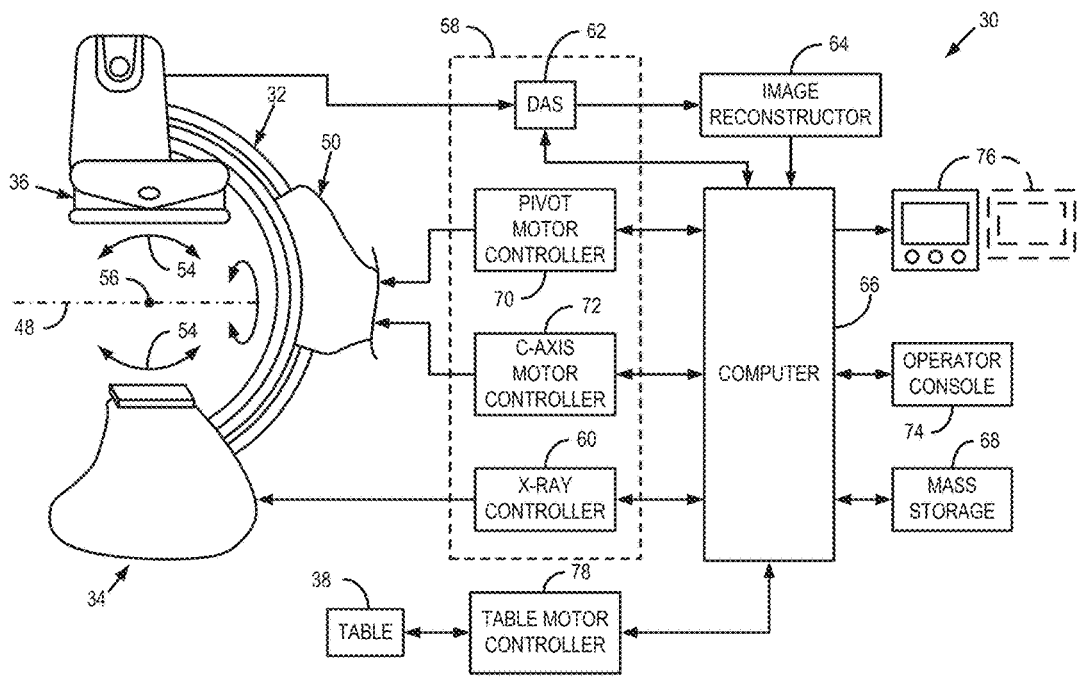
FIG. 2B is a block diagram of the system of FIG. 2A

Referring now to FIGS. 2A and 2B, an example of the angiographic imaging system 12 may include an x-ray imaging system 30. The x-ray imaging system 30 is illustrated as a so-called "C-arm" imaging system; however, other geometries may be used to acquired x-ray angiographic images. For example, any of a variety of x-ray imaging systems capable of acquiring data to create a 4D-DSA image may be used, including systems that acquire time-resolved 2D images using a single plane x-ray system.

The imaging system 30, as illustrated, may be generally designed for use in connection with interventional procedures. The imaging system 30 is characterized by a gantry 32 forming a C-arm that carries an x-ray source assembly 34 on one of its ends and an x-ray detector array assembly 36 at its other end. The gantry 32 enables the x-ray source assembly 34 and detector array assembly 36 to be oriented in different positions and angles around a patient disposed on a table 38, while enabling a physician access to the patient.

The gantry includes a support base 40, which may include an L-shaped pedestal that has a horizontal leg 42 that extends beneath the table 38 and a vertical leg 44 that extends upward at the end of the horizontal leg 42 that is spaced from of the table 38. A support arm 46 is rotatably fastened to the upper end of vertical leg 44 for rotation about a horizontal pivot axis 48. The pivot axis 48 is aligned with the centerline of the table 38 and the support arm 46 extends radially outward from the pivot axis 48 to support a drive assembly 50 on its outer end. The C-arm gantry 32 is slidably fastened to the drive assembly 50 and is coupled to a drive motor (not shown) that slides the C-arm gantry 32 to revolve it about a C-axis 52, as indicated by arrows 54. The pivot axis 48 and C-axis 52 intersect each other at an isocenter 56 that is located above the table 408 and they are perpendicular to each other.

The x-ray source assembly 34 is mounted to one end of the C-arm gantry 32 and the detector array assembly 36 is mounted to its other end. As will be discussed in more detail below, the x-ray source assembly 34 includes an x-ray source (not shown) that emits a beam of x-rays, which are directed at the detector array assembly 36. Both assemblies 34 and 36 extend radially inward to the pivot axis 38 such that the center ray of this cone beam passes through the system isocenter 56. The center ray of the x-ray beam can, thus, be rotated about the system isocenter 56 around either the pivot axis 38, the C-axis 52, or both during the acquisition of x-ray attenuation data from a subject placed on the table 38.

As mentioned above, the x-ray source assembly 34 contains an x-ray source that emits a beam of x-rays when energized. The center ray passes through the system isocenter 56 and impinges on a two-dimensional flat panel digital detector housed in the detector assembly 36. Each detector element produces an electrical signal that represents the intensity of an impinging x-ray and, hence, the attenuation of the x-ray as it passes through the patient. During a scan, the x-ray source and detector array are rotated about the system isocenter 56 to acquire x-ray attenuation projection data from different angles. By way of example, the detector array is able to acquire thirty projections, or views, per second. Generally, the numbers of projections acquired per second is the limiting factor that determines how many views can be acquired for a prescribed scan path and speed. Accordingly, as will be described, this system or others can be used to acquire data that can be used to crate 4D DSA image data sets that may provide 3D angiographic volumes at the rate of, for example, 30 per second. As will be further described, such 4D DSA images may be augmented with flow or velocity information.

Referring particularly to FIG. 2B, the rotation of the assemblies 34 and 36 and the operation of the x-ray source are governed by a control system 58 of the imaging system 30. The control system 58 includes an x-ray controller 60 that provides power and timing signals to the x-ray source. A data acquisition system (DAS) 62 in the control system 58 samples data from detector elements in the detector array assembly 36 and passes the data to an image reconstructor 64. The image reconstructor 64, receives digitized x-ray data from the DAS 62 and performs image reconstruction. The image reconstructed by the image reconstructor 64 is applied as an input to a computer 66, which stores the image in a mass storage device 68 or processes the image further.

The control system 58 also includes pivot motor controller 70 and a C-axis motor controller 72. In response to motion commands from the computer 66, the motor controllers 70 and 72 provide power to motors in the imaging system 30 that produce the rotations about the pivot axis 38 and C-axis 52, respectively. A program executed by the computer 66 generates motion commands to the motor controllers 70 and 72 to move the assemblies 34 and 36 in a prescribed scan path.

The computer 66 also receives commands and scanning parameters from an operator via a console 74 that has a keyboard and other manually operable controls. An associated display 76 or displays allows the operator to observe the reconstructed image and other data from the computer 66. The operator supplied commands are used by the computer 66 under the direction of stored programs to provide control signals and information to the DAS 62, the x-ray controller 60, and the motor controllers 70 and 72. In addition, the computer 66 operates a table motor controller 78, which controls the patient table 408 to position the patient with respect to the system isocenter 56.

Figure 3:
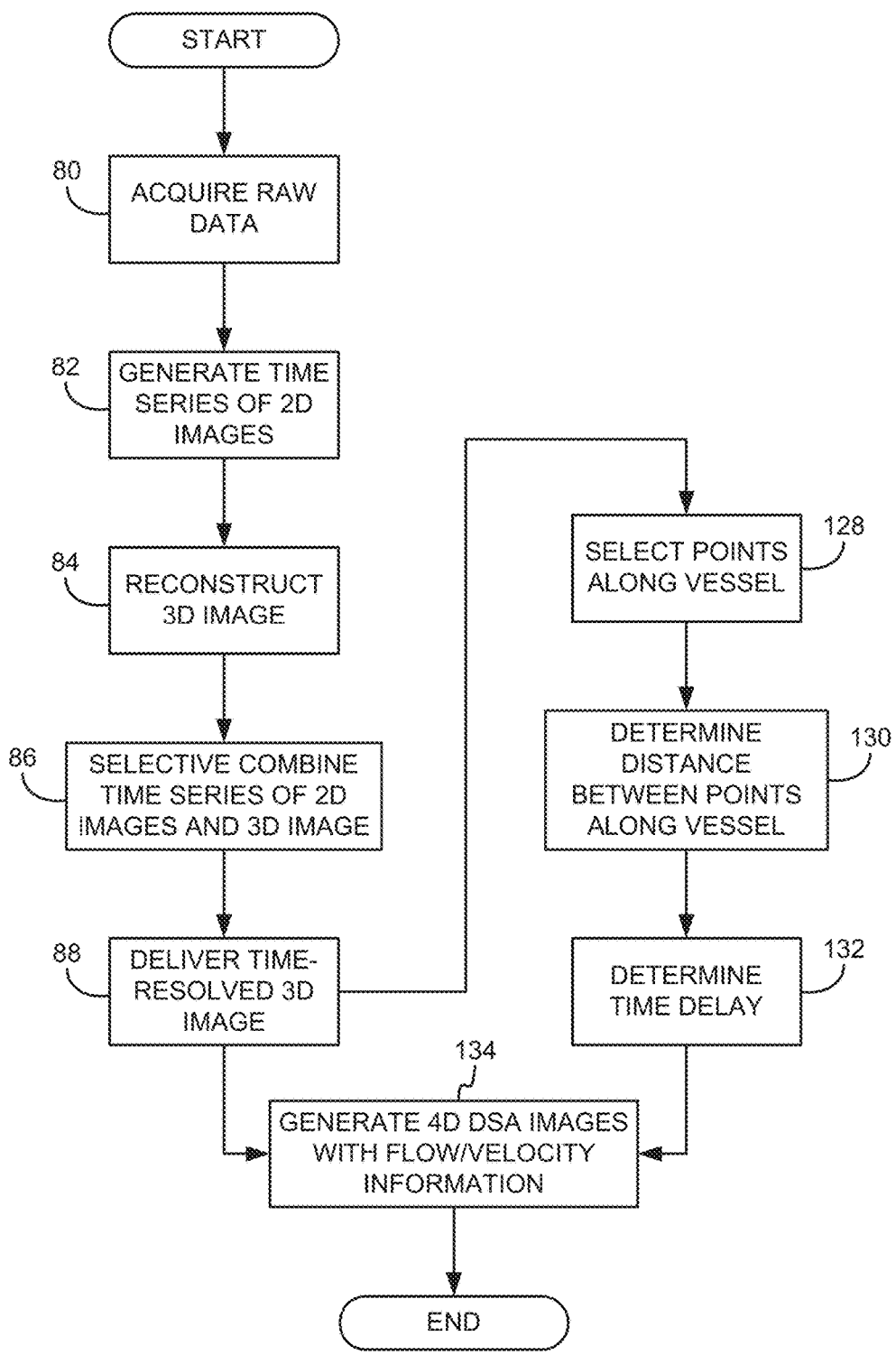
FIG. 3 is a flow chart setting forth examples of steps for producing a 4D DSA image including flow information in accordance with the present disclosure.

The above-described system can be used to acquire raw angiographic data that can then be processed to generate a time-resolved 3D angiographic image in the form of a 4D DSA image. Referring to FIG. 3, a process for creating a 4D DSA image begins at process block 80 with the acquisition of image data from a region-of-interest in a subject using a medical imaging system, such as a CT system or a single-plane, biplane, or rotational x-ray systems. At process block 82, a time-series of 2D images is generated from at least a portion of the acquired image data. While the time-series of 2D images can have a high temporal and spatial resolution and may include images acquired at different angles around the subject, it generally cannot provide a sophisticated 3D depiction of the subject. At process block 84, a 3D image of the subject is reconstructed from the acquired image data. Though individual projections used to reconstruct this 3D image may themselves convey some degree of temporal information, the reconstructed 3D image itself is substantially free of temporal resolution. For brevity, the 3D image substantially without temporal resolution and the time-series of 2D images may simply be referred to as the "3D image" and "2D images," respectively.

At process block 86, the time-series of 2D images and the static 3D image are selectively combined so that the temporal information included in the 2D images is imparted into the 3D image. This results in the production of a time-resolved 3D image of the subject with high temporal and spatial resolution that is delivered at process block 88. While the selective combination process varies based on the medical imaging system used and the nature of the acquired image data, it generally involves the steps of (1) registering the 2D images to the 3D image, (2) projecting the attenuation value of the pixels in the 2D images into the 3D image, and (3) weighting the 3D image with the projected values for each individual frame of the time-series of 2D images. It is contemplated that the temporal weighting in step (3) generally involves multiplying the projected pixel values with the 3D image. These three steps, which can be referred to as "multiplicative projection processing" (MPP), may be accompanied by additional steps to improve image quality or reduce the prevalence of errors and artifacts. For example, the intensity values of pixels and voxels in the 2D images and 3D image produced at process blocks 82 and 84 may quantify an x-ray attenuation level at a given location in the subject. These attenuation levels may not be preserved when multiplying the 3D image with projected pixel values. Accordingly, more accurate indications of the attenuation levels may be restored using the intensity value at each voxel in the time-resolved 3D image, for example, by taking the n-th root, if (n−1) different sets of 2D images are used, to weight the 3D image.

The 2D images and 3D image produced at process blocks 82 and 84, respectively, can be produced using DSA techniques. That is, 2D images depicting the subject's vasculature can be produced by reconstructing image data acquired as a bolus of contrast passes through the vasculature and subtracting out a pre-contrast, or "mask," image acquired before the administration of contrast agent. Likewise, a 3D image of the same vascular structures can be produced by reconstructing image data acquired as contrast agent occupies the vasculature and subtracting out a mask image to remove signal associated with non-vascular structures. The time-resolved 3D image produced by combining the DSA images depicts the subject's vascular structures with both excellent spatial and excellent temporal resolution and may thus be referred to as a 4D-DSA image. As used herein, this time-resolved 3D image may also be referred to as a 4D image, a 4D angiographic image, or a 4D DSA image. The 4D-DSA images can be displayed as "pure" arterial, pure venous, or composite arterial and venous images and can be fully rotated during each state of the filling of the vasculature, thereby enabling greatly simplified interpretation of vascular dynamics. The spatial resolution of these 4D-DSA images may be on the order of $512^3$ pixels at about 30 frames per second. This represents an increase over traditional 3D-DSA frame rates by a factor between 150 and 600, without a significant image quality penalty being incurred. Further discussion of 4D DSA techniques may be found in U.S. Pat. No. 6,643,642, which is incorporated herein by reference in its entirety. Also, U.S. Pat. No. 8,768,031 is incorporated herein by reference, which extends the 4D DSA imaging process to use time-independent 3D rotational DSA volumes. Furthermore, US Published Patent Application US2013/0046176, which describes the use of dual-energy x-ray imaging with 4D DSA, is incorporated herein by reference.

Figure 4:
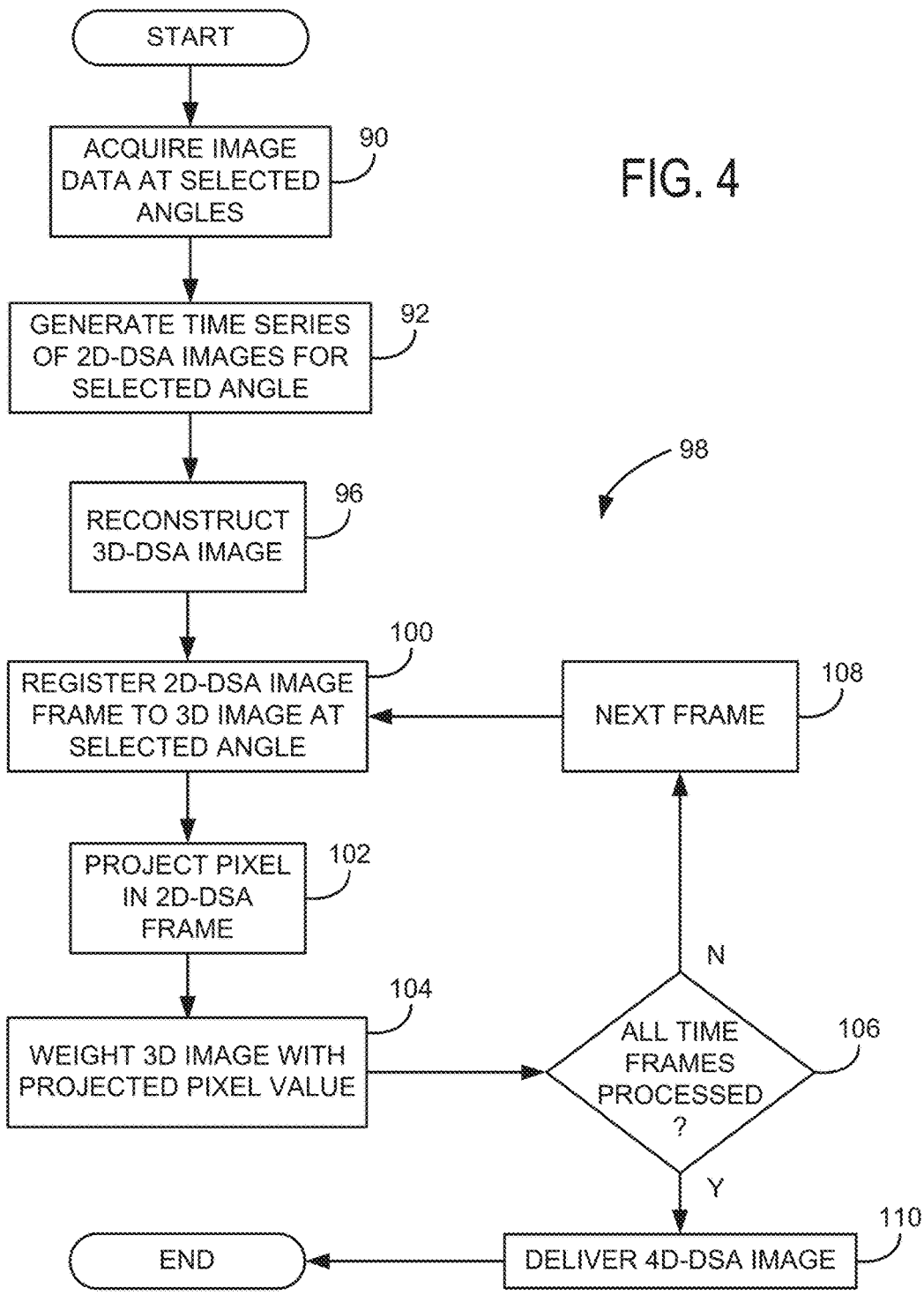
FIG. 4 is a flow chart setting forth further examples of steps for producing a 4D DSA image from x-ray data.

Referring to FIG. 4, a more specific implementation of the above-described process can be employed to produce a 4D-DSA image of a subject using a single-plane x-ray system in combination with a rotational x-ray system or CT system. In this case, the process begins at process block 90, when time-resolved image data from a ROI in the subject is acquired using the single-plane system following the administration of a contrast agent to the subject. Using the above-discussed DSA techniques, a time-series of 2D-DSA images at selected angles about the ROI is generated at process block 92. These 2D-DSA images depict the contrast agent passing through and enhancing arterial structures in the ROI. The 2D-DSA images are substantially free of signal from non-vascular structures, as well as signal from venous structures can be excluded due to the high temporal resolution of the 2D acquisition. A 3D-DSA image is reconstructed at process block 96 from the acquired image data. Specifically, the projections acquired at process block 90 may be log subtracted from those acquired in a non-contrast mask sweep. Typically, vascular structures in the 3D-DSA image are substantially opacified due to the use of contrast agent and the time necessary for data acquisition.

Figure 5:
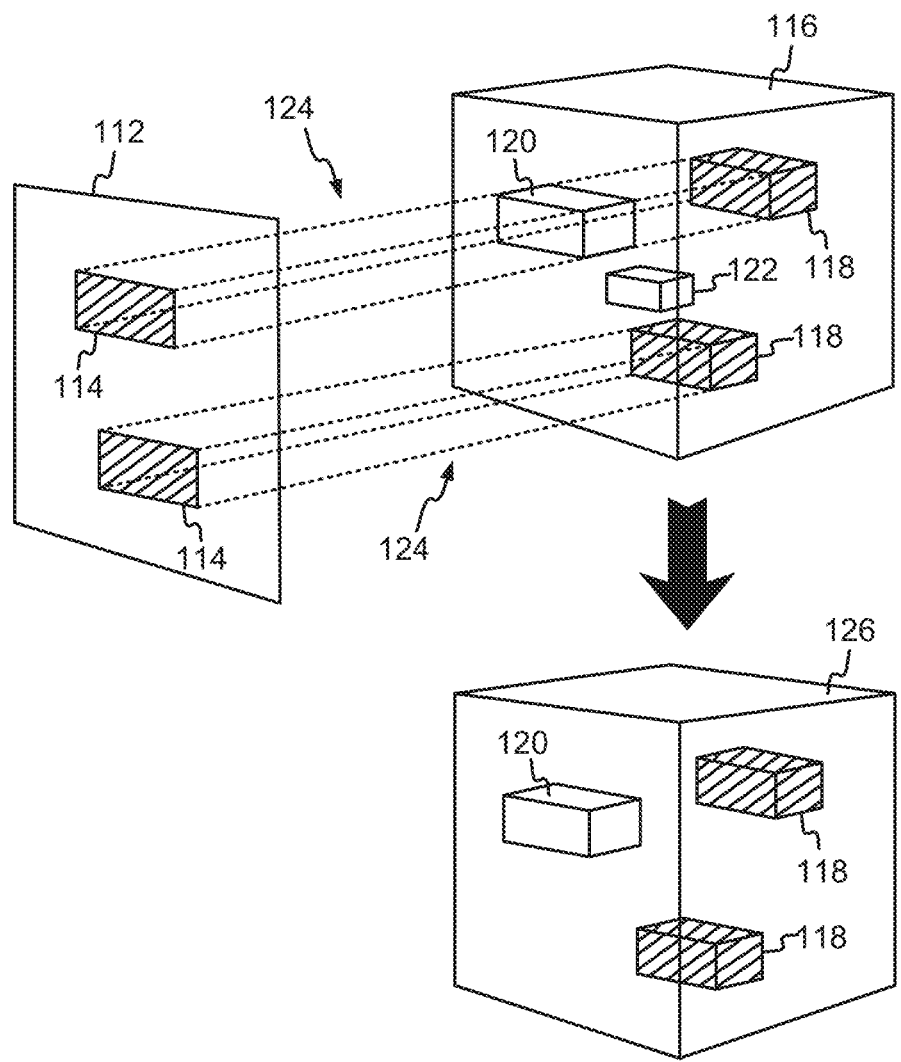
FIG. 5 is a graphic depiction of selective combination of a 3D image with a 2D DSA image frame to produce 4D DSA data.

Referring now to FIGS. 4 and 5, the images produced thus far can be selectively combined with the steps indicated generally at 98 to produce a 4D-DSA image with the detailed 3D resolution of the 3D-DSA image and the temporal resolution of the time-series of 2D-DSA images. In the exemplary depiction of the selective combination process provided in FIG. 5, a single frame of the time-series of 2D-DSA images 112 includes two image regions having arterial signal 114, while the 3D-DSA image 116 includes both arterial signal 118 and venous signal 120 and 122. At process block 100 of FIG. 4, a frame of the 2D-DSA image 112 is registered to the 3D-DSA image 116 at the selected angle and, at process block 102, the values of the pixels in the 2D-DSA frame are projected along a line passing through each respective pixel in a direction perpendicular to the plane of the 2D-DSA frame. The projection of pixels with arterial signal 114 into the 3D-DSA image is indicated generally at 124. For simplicity, the projection of pixels in the 2D-DSA frame with no contrast is not shown. At process block 104 of FIG. 4, the 3D-DSA image 116 is weighted by the values projected from the 2D-DSA frame 112 to produce the 4D-DSA image 126. This may include multiplying the projected values with the voxels of the 3D image that they intersect. The weighting process results in the preservation of the arterial signal 118 and the exclusion, or "zeroing-out," of undesired venous signal 122 in the 4D-DSA image. In addition, the intensity value of the arterial signal 114 in the 2D-DSA frame is imparted into the 3D arterial signal volume 118, thereby allowing the changes in arterial signal over time captured by the 2D-DSA images to be characterized in the 4D-DSA image. At decision block 106 of FIG. 4, if all of the frames have yet to be processed, the process moves to the next frame of the time-series of 2D-DSA images at process block 108 and repeats the selective combination process generally designated at 98. This cycle continues until, at decision block 106, it is determined that a 4D-DSA image has been generated for all relevant time frames. The 4D-DSA image can thus be delivered at process block 110.

The venous signal 120 preserved in the 4D-DSA image 126 illustrates a potential challenge when generating 4D images using only a single time-series of 2D images acquired at a single angle. That is, signal from desired structures, such as the arterial signal 114 in this example, can inadvertently be deposited in 3D voxels representing undesired structures, such as the venous region 120 in this example. The unwanted structures can thus be preserved in the 4D image as "shadow artifacts" when their signal lies along the projected values of a desired structure in a dimension inadequately characterized by the time-series of 2D images. This can result, for example, in a 4D-DSA image in which desired arterial structures are obscured by undesired venous structures for some time frames. However, this will cause a temporary anomaly in the contrast versus time course for the vein. If the time frames of the 4D-DSA image are analyzed, this anomaly can be recognized as inconsistent with the general waveform of the vein and the vein can be suppressed in the time frame where the projected arterial signal is strong. Accordingly, temporal parameters such as mean transit time (MTT) or time-to-fractional-peak can be calculated for each voxel and this information can be used to clean up shadow artifacts. To assist an operator in identifying shadow artifacts and temporal irregularities, the temporal parameters can be color-coded and superimposed on the 4D-DSA image delivered at process block 110 of FIG. 4. The temporal parameters can also be exploited to infer information related to potential perfusion abnormalities in the absence of direct perfusion information from parenchymal signal. Further still and as will be described in detail, dynamic physiological information, such as velocity information, can be determined from the acquired data.

The acquisition of contrast enhanced image data can be performed following the administration of contrast agent to the subject via either IV or IA injection. When scanning a local area, IA injections allow high image quality and temporal resolution as well as reduced contrast agent dose. However, IV injections are often more suitable for scanning larger regions where multiple IA injections at different locations and different arteries would otherwise be required.

Regardless of whether the contrast agent is introduced as an IV or IA injection, systems and methods for utilizing information about the time of arrival (TOA) of the contrast agent can be used to provide flow or velocity data along with the 4D DSA images. For example, co-pending U.S. patent application Ser. No. 14/643,853, filed Mar. 10, 2015, describes such a system and method and is incorporated herein by reference in its entirety. These systems and methods can determine blood velocity and flow from 4D DSA data based on TOA information and, specifically, a mean transit time calculation for each point along a vessel. The inverse slope of this mean transit time provides the mean velocity in the vessel.

As will be described, the present disclosure provides a system and method that can deliver 4D DSA images including information about dynamic physiological characteristics of the structures that are spatially and temporally resolved in the 4D DSA images. That is, while 4D DSA images, by definition, are spatially resolved in three dimensions and also temporally resolved, the present disclosure provides systems and methods to provide further information to a clinician that can be coupled with the 4D DSA images, for example, to communicate flow or velocity information within the 4D DSA images. Furthermore, the present disclosure can derive information about the dynamic physiological characteristics, such as flow direction or velocity, from the 4D DSA data. For example, as will be described, the systems and methods of the present disclosure can derive pulsatile waveforms, such as generated by the pulsatile flow of blood through vessels or artificially created by dynamic injections, from the subject being studied and use the pulsatile waveforms, as well as the time-resolved three dimensional information regarding the vessel to derive dynamic physiological information, such as flow direction or velocity, without relying on TOA information.

Traditional DSA or non-time-resolved, three-dimensional (3D) imaging techniques can fail when attempting to determine a distance, such as $\Delta x$, or time shift, such as $\Delta t$, relative to a given vessel. Obviously, if the imaging data or the technique used to acquire the data lacks temporal information, such as is generally the case with traditional computed tomography angiography (CTA), it is not possible to determine a time shift, $\Delta t$. Furthermore, even if temporal information is available, such as when using traditional DSA, it can be difficult to accurately determine a distance, $\Delta x$, using a maximum intensity projection (MIP). That is, a MIP or other, non-4D image, may not allow one to correctly estimate the length of path along a given vessel, such as when the vessel extends along a circuitous path within the plane of the projection. However, using the systems and methods of the present disclosure, it is possible to correctly estimate the path length along the vessels and, using systems and methods that will be described, using a selected distance along a given vessel to determine phase shifts that can be correlated with flow direction or velocity within the vessel.

As will be described, the systems and methods of the present disclosure can consider two different points along a vessel separated by a distance, $\Delta x$ and determine a pulsatile waveform that is delayed in time by an amount $\Delta t$ across the distance, $\Delta x$. The systems and methods of the present disclosure can use the time shift to then determine the flow direction and/or velocity using $\Delta x$ and $\Delta t$. This information can be coupled with the 4D DSA images to provide a clinician with valuable dynamic, physiological information.

Figure 6:
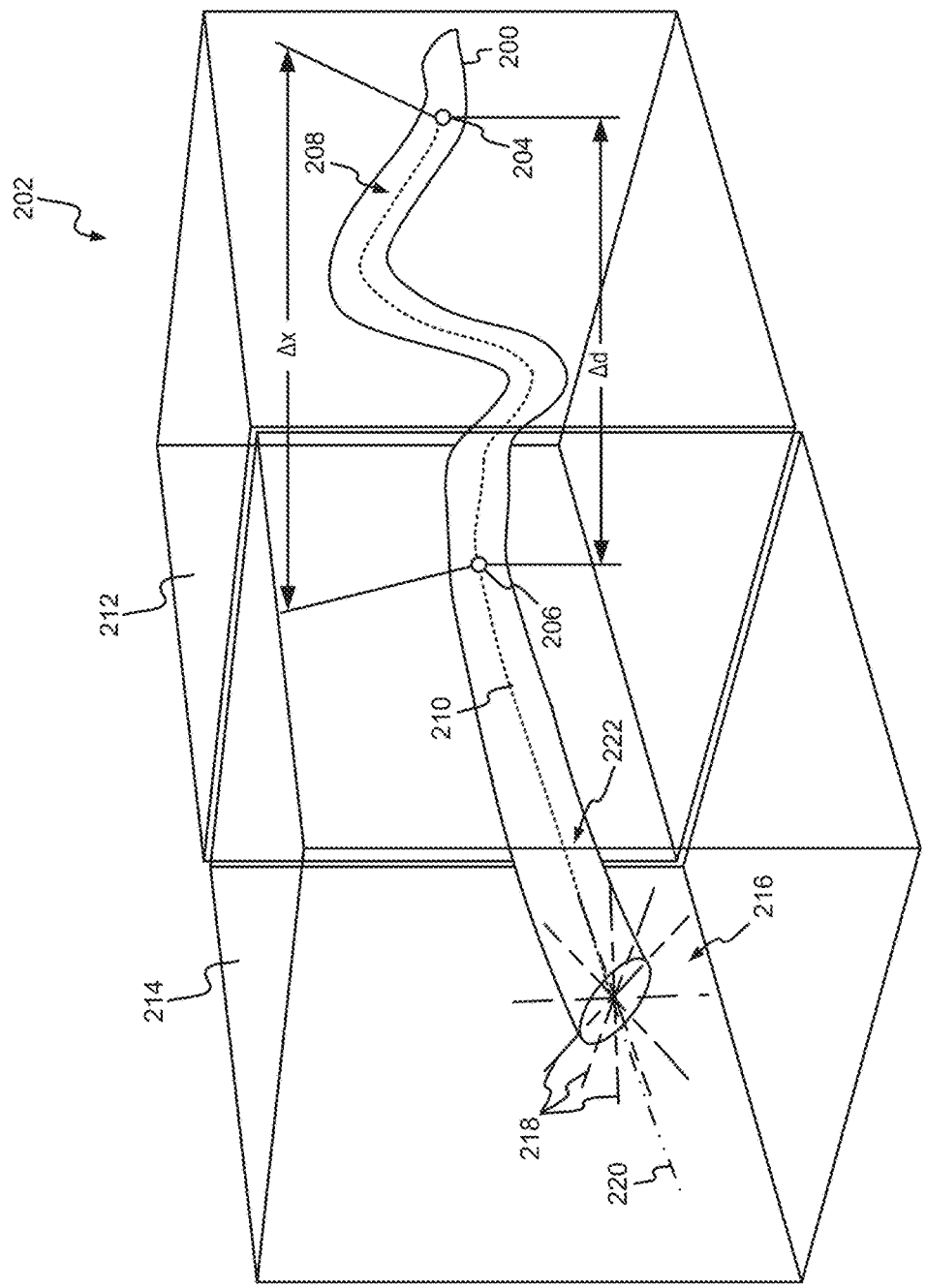
FIG. 6 is a graphic illustration of a vessel taken from a 4D angiographic volume of images.

Specifically, referring to FIG. 3, at process block 128 points are selected that are displaced from one another along a vessel in the 4D DSA images. At process block 130, the distance between the selected points along the vessel can be determined. For example, referring to FIG. 6A, a vessel 200 is illustrated that extends along a circuitous route through a three dimensional space 202, which can be resolved in three dimensions and time via a 4D DSA image created as described above. Using the information available in a 4D DSA dataset, two points 204, 206 can be selected that are separated along the vessel 200 by a distance, $\Delta x$, along a path 208 through the vessel 200, which as will be described, may follow a centerline 210 of the vessel. Despite the path 208 being curved and, thus, having a distance, $\Delta x$, that is greater than an absolute distance, $\Delta d$, separating the two points 204, 206, the use of 4D DSA data allows the distance, $\Delta x$, along a path 208 through the vessel 200 to be determined.

As one non-limiting example, a marching cubes algorithm may be used to determine a centerline 210 of the vessel 200. In doing so, a series of marching cubes 212, 214 may used to find the order and position of points along the centerline 210 of the vessel 200. Alternatively, a wider range of vessels and associated velocities may be processed automatically using a rotating mask process, which may rotate in 3D. This rotating mask algorithm uses rotating binary masks 216 to determine the direction of the centerline 210 by positioning a plurality of masks 218 along a potential centerline 220 and calculating a probability measure for each pixel that a given mask 218 is aligned with the potential centerline 220. The mask 218 is rotated in 3D to find the orientation that has the highest correlation with the local centerline 222.

Referring again to FIG. 3, with distance, $\Delta x$, between the points along the vessel determined, a variety of parameters may be calculated. For example, the time-resolved, 3D image data (4D DSA data) can be used to determine a diameter of the vessel. Also, the 4D DSA data can be used to determine a time delay, $\Delta t$, at process block 132. Determining the time delay, $\Delta t$, at process block 132 may be achieved using a variety of methods. For example, pulsatility through the vessel may be used as a mechanism to discern time delays.

Figure 7A:
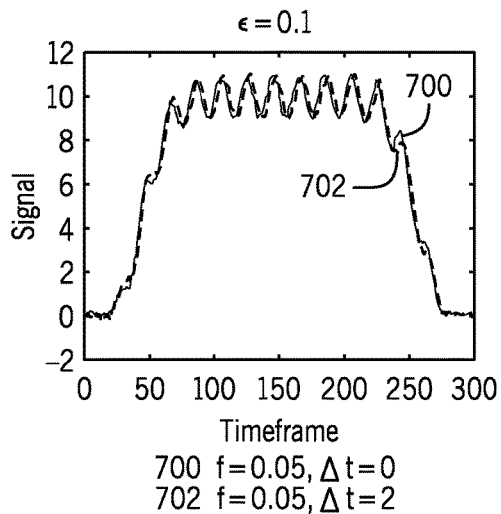
FIG. 7A is a graph showing pulsatility waveforms for two points selected in the vessel of FIG. 6.
Figure 7B:
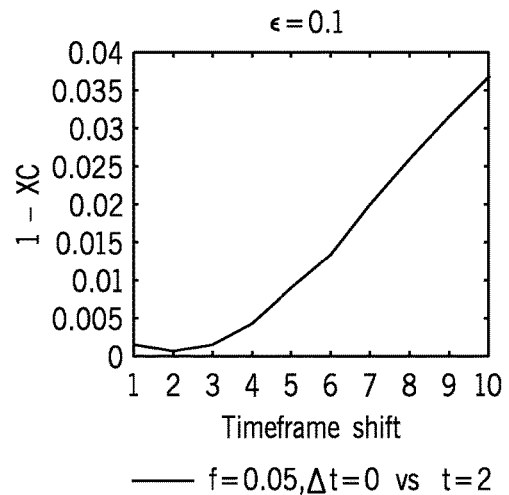
FIG. 7B is a graph showing a cross correlation versus integer time frame shift for the waveforms illustrated in FIG. 7A.
Figure 7C:
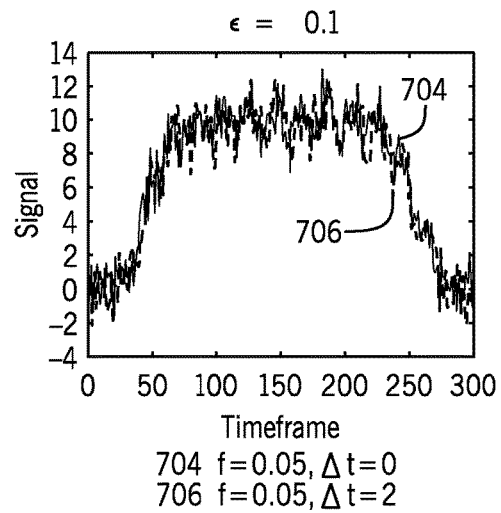
FIG. 7C is a graph showing the pulsatility waveforms of FIG. 7A with increased noise.
Figure 7D:
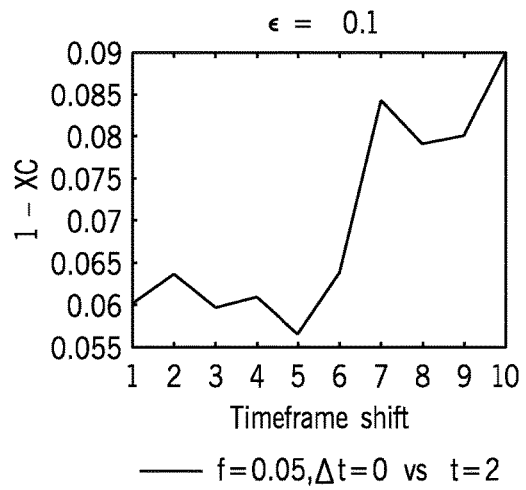
FIG. 7D is a graph showing a cross correlation versus integer time frame shift for the waveforms illustrated in FIG. 7C.

In particular, referring to FIG. 7A, once the two 204, 206 are selected, respective time attenuation curves 700, 702 with pulsatile flow can be derived from the 4D DSA data. As illustrated in FIG. 7B, a check of the similarity of the curves 700, 702 of FIG. 7B using cross correlation versus integer time frame shift shows a strong cross correlation, despite noise in two such similar curves 700, 702. The minimum 703 in the comparison curve versus the temporal shift value of FIG. 7B gives the $\Delta t$ value that, when combined with $\Delta x$, provides the velocity of flow between the two selected points. However, as illustrated in FIGS. 7C and 7D, as the noise increases in curves 704, 706, the resulting time-shift estimate can become unreliable, as illustrated in FIG. 7D.

To overcome such noise, Fourier analysis can be performed to concentrate on the pulsatile frequency. Taking the Fourier transform of the two temporal waveforms 704, 706 allows one to identify the peak corresponding to the fundamental frequency of the pulsatility or a harmonic thereof, such as the first harmonic. For each of the Fourier transform peaks corresponding to the two points on the vessel, the phase of the Fourier transform can then be calculated.

Figure 7E:
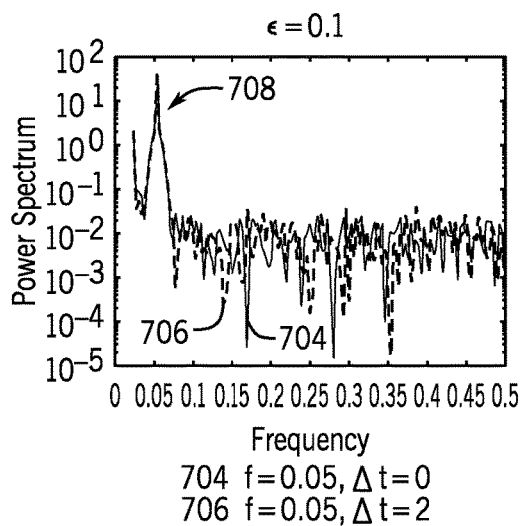
FIG. 7E is a graph showing the power spectrum of the waveforms of FIG. 7A.

Turning to FIG. 7E, the present disclosure recognizes that the power spectrum contains a peak 708 at the characteristic frequency ($f_k$) of pulses considered over a window or number of pulses (N):

$$PS \sim \frac{|f_k|^2}{N}. \qquad \text{Eqn. (1)}$$

To determine the time shift, $\Delta t$, the FFT phases are inspected at a select frequency index corresponding to pulses, where the frequency relates to the phase ($\Phi$) as:

$$f_k = |f_k|e^{i\phi} \qquad \text{Eqn. (2);}$$

The phase is related to the temporal displacement through the Fourier shift theorem such that the time shift, $\Delta t$, is given by:

$$\Delta t = (\phi_1 - \phi_2)\frac{1}{2\pi f}; \qquad \text{Eqn. (3)}$$

where f is the characteristic pulsation frequency and $\phi_1$ and $\phi_2$ is the phase at the respective selected points. With the distance, $\Delta x$, and the time shift, $\Delta t$, of a signal, for example pulsatility, as it traverses the distance, $\Delta x$, velocity can be readily calculated as a vector pointing along the determined centerline in the direction of flow at a speed of $\Delta x/\Delta t$. That is, the sign (positive or negative) of $\Delta t$ indicates the direction of flow along the vessel (i.e., from the point associated with $\phi_i$ to the point associated with $\phi_2$, or vice versa). The absolute value of $\Delta t$ indicates the speed of the flow. Thus, velocity, a vector, can be provided with the 4D DSA images to show the speed and direction of flow in a vessel.

Figure 7F:
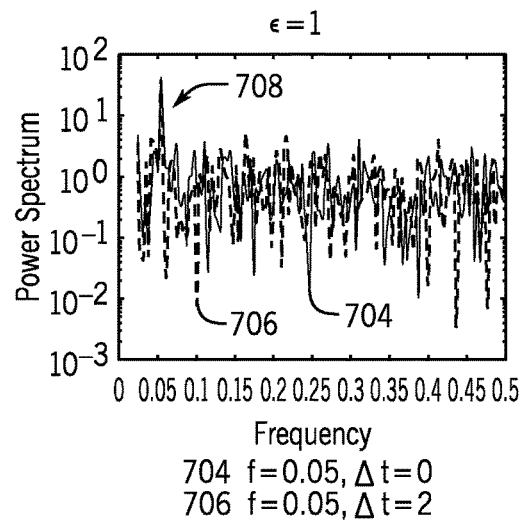
FIG. 7F is a graph showing the power spectrum of the waveforms of FIG. 7C.
Figure 7G:
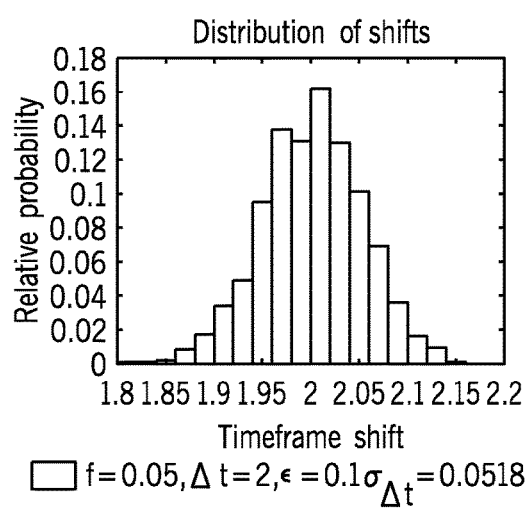
FIG. 7G is a bar graph showing the relative probability of a distribution of shifts illustrating that, even in the face of substantial noise, the time shift can be predictably determined within a reasonable tolerance.
Figure 7H:
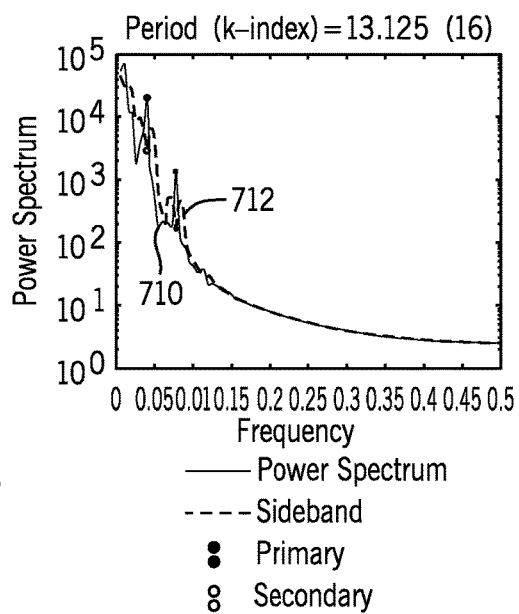
FIG. 7H is a graph of the power spectrum showing a trial point in the power spectrum compared with the average of the sideband taken to be the nearest 4 frequency points.

Referring now FIG. 7F, it can be seen that the FFT power spectrum peak 708 is still significant and distinguishable in face of substantial noise in the time attenuation curves 704, 706. Furthermore, the phase information generally preserved at the peak of the FFT power spectrum 708. That is, as illustrated in FIG. 7G, even in the face of very large noise, the phase information can be discerned and, thus, as will be described, the estimates of the timeframe shift, albeit with uncertainty, can be determined. The above-derived $\Delta t$, when combined with the above-determined $\Delta x$ enables the calculation of flow velocity.

Figure 7I:
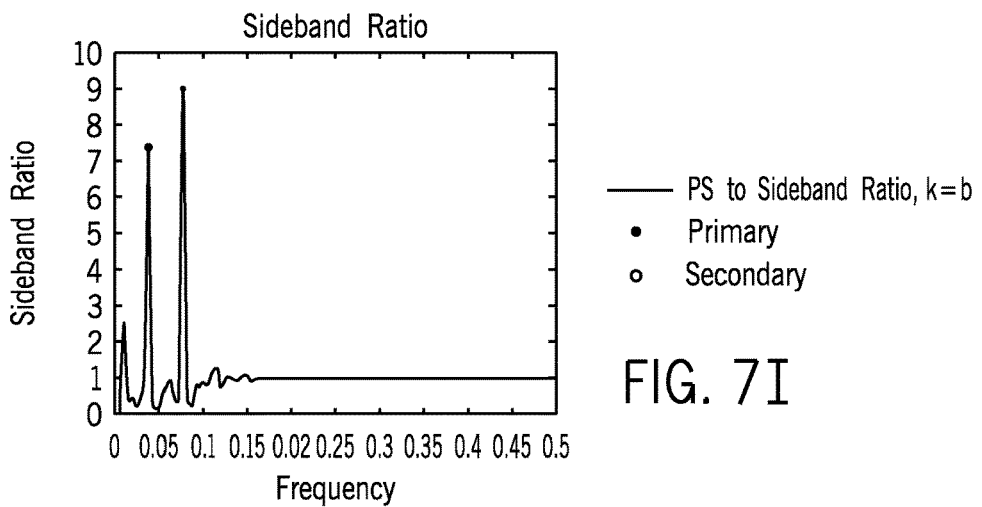
FIG. 7I is a graph of sideband ratio derived from FIG. 7H and showing the prominent peaks.
Figure 7J:
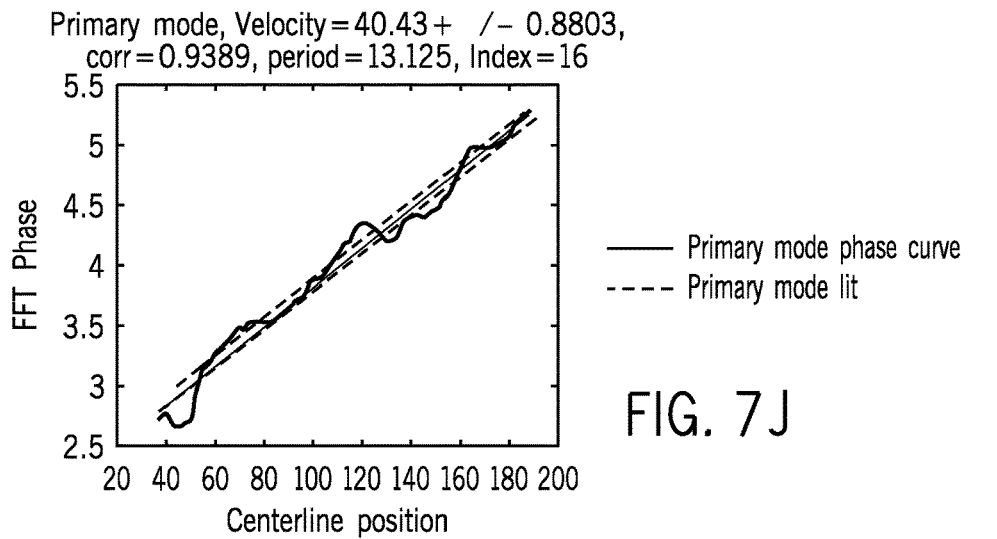
FIG. 7J is a graph of phase versus centerline position showing strong correlation for velocity in the primary mode.
Figure 7K:
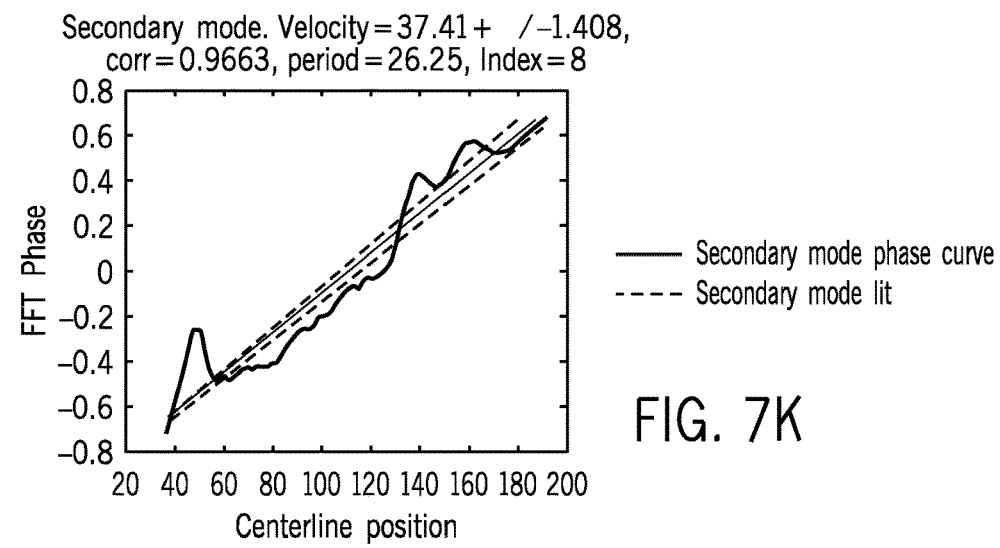
FIG. 7K is a graph of phase versus centerline position showing strong correlation for velocity in the secondary mode.

In addition to the characteristic or fundamental frequency, as mentioned, a harmonic may be used. Referring to FIG. 7H-7K, the pulsatile frequency can be selected by using a sideband analysis in which a trial point in the power spectrum 710 is compared with the average of the sideband 712, for example, taken to be the nearest 4 frequency points (two on each side). This ratio highlights the prominent peaks and is shown in FIG. 7I. Therefore, the comparison of the power spectrum at f_0 and the sideband around f_0 is a useful metric for selecting candidate frequencies. Both the fundamental and harmonic show a velocity that is in the 40 cm/s range. As illustrated in FIGS. 7J and 7K, respectively, the primary mode and the secondary mode produce reliable velocity estimates. Furthermore, performing the same analysis with flow instead of speed can be used to improve the reliability of flow estimates. Though the fundamental frequency and the first harmonic are described above, other, higher harmonics may also be used. In some cases, the fundamental pulsatile frequency and higher harmonics can be combined to form a velocity or flow measurement using a weighted average of the candidate frequencies, with a weighting assigned by their respective sideband ratios.

The above-described correlation/shift method can also be applied to determine the optimal spatial shift required to line up the signal versus distance curves at two points in time. That is, one can choose two time points and look at the spatial distribution at these two points in time and then determine the spatial shift required to line up the two spatial distributions using cross correlation, sum of squares, or other analysis. This method also provides a Δx and Δt from which velocity or flow can be calculated.

Referring again, to FIG. 3, once the Δx and Δt have been determined, the flow/velocity information can be combined with the time-resolved 3D images generated at process block 88 to deliver 4D DSA images with flow/velocity information included. For example, the 4D DSA images may be color coded or animated to provide a spatially- and time-resolved report to a clinician that also includes information about the underlying dynamic physiological performance, such as through flow direction or velocity.

EXAMPLE

Figure 8A:
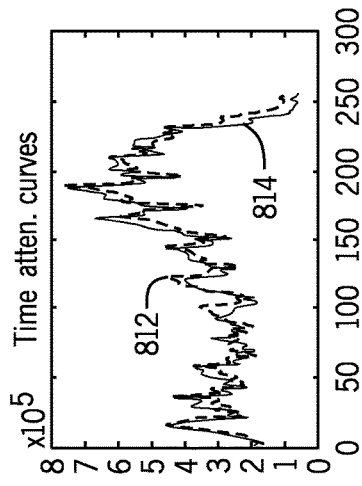
FIG. 8A is an image frame taken from a 4D DSA set showing a vessel having selected points along one branch.
Figure 8B:
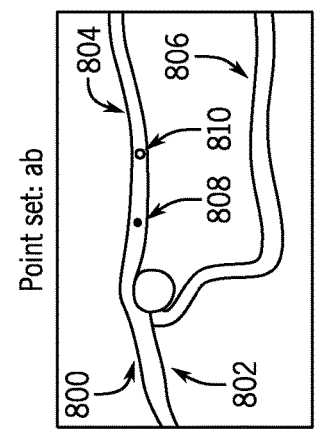
FIG. 8B is a graph showing pulsatility waveforms associated with the selected points of FIG. 8A.
Figure 8C:
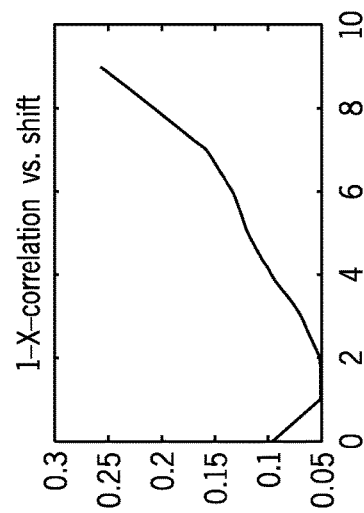
FIG. 8C is a graph of the power spectrum of the waveforms of FIG. 8B.
Figure 8D:
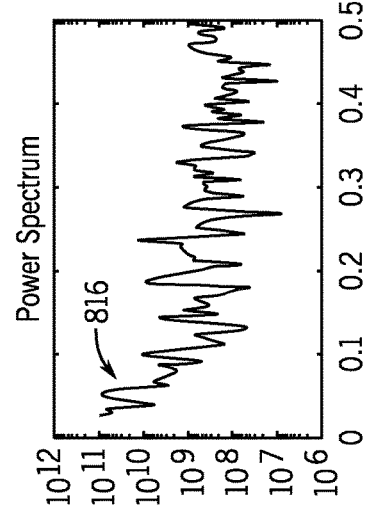
FIG. 8D is a graph of a cross correlation versus integer time frame shift for the waveforms illustrated in FIG. 8B.

Referring to FIG. 8A a static image selected from a 4D DSA image set is illustrated. In the image, a vessel 800 is shown that has multiple branches 802, 804, 806. Two points 808, 810 have been selected in the image. As shown in FIG. 8B, the respective waveforms 812, 814 from the selected points 808, 810 of FIG. 8A can be derived and, as shown in FIG. 8C, the power spectrum can be derived. The power spectrum has a discernible peak 816. However, in this case, since the waveforms 812, 814 were not obscured by noise, the cross-correlation versus shirt shows a clear minimum. The minimum in the comparison curve versus the temporal shift value gives the Δt that, when combined with Δx, provides the velocity.

Referring now to FIG. 8E, the same vessel 800 as shown in FIG. 8A is illustrated. However, two different points 818, 820 in another branch 806 of the vessel 800 have been selected. As such, FIG. 8F shows the waveforms associated with the points 818, 820 selected in FIG. 8E. Likewise, FIG. 8G provides the power spectrum associated with the points 818, 820 selected in FIG. 8E. Finally, FIG. 8H shows the minimum in the comparison curve versus the temporal shift value gives the Δt that, when combined with Δx, provides the velocity.

Figure 8I:
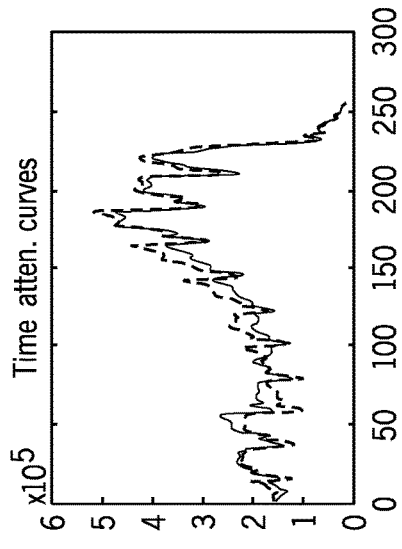
FIG. 8I is an image frame taken from a 4D DSA set showing the vessel of FIGS. 8A and 8E having another two selected points along still another branch.
Figure 8J:
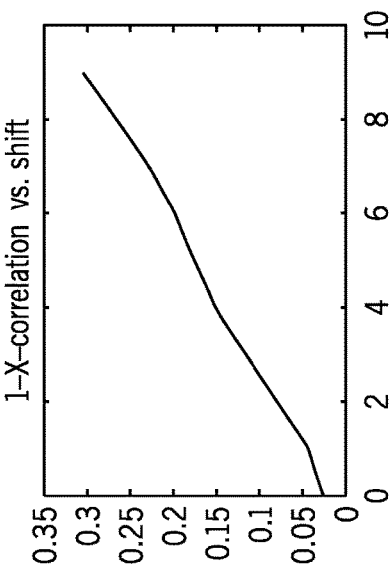
FIG. 8J is a graph showing pulsatility waveforms associated with the selected points of FIG. 8I.
Figure 8K:
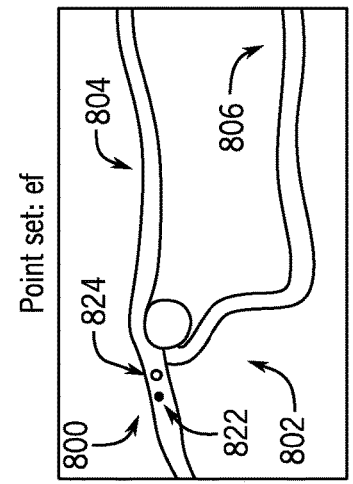
FIG. 8K is a graph of the power spectrum of the waveforms of FIG. 8J.
Figure 8L:
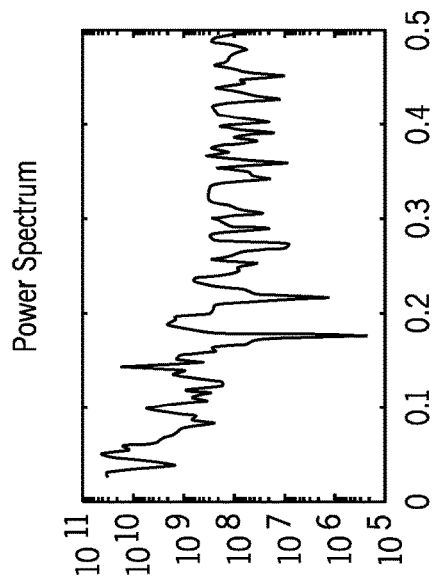
FIG. 8L is a graph of a cross correlation versus integer time frame shift for the waveforms illustrated in FIG. 8J.

Referring to FIG. 8I, again, the same vessel 800 as shown in FIGS. 8A and 8E is illustrated, with yet two different points 822, 824 in another branch 802 of the vessel 800 selected. As such, FIG. 8J shows the waveforms associated with the points 822, 824 selected in FIG. 8I. Likewise, FIG. 8K provides the power spectrum associated with the points 822, 824 selected in FIG. 8I. Finally, FIG. 8L shows the minimum in the comparison curve versus the temporal shift value gives the Δt that, when combined with Δx, provides the velocity.

Figure 8M:
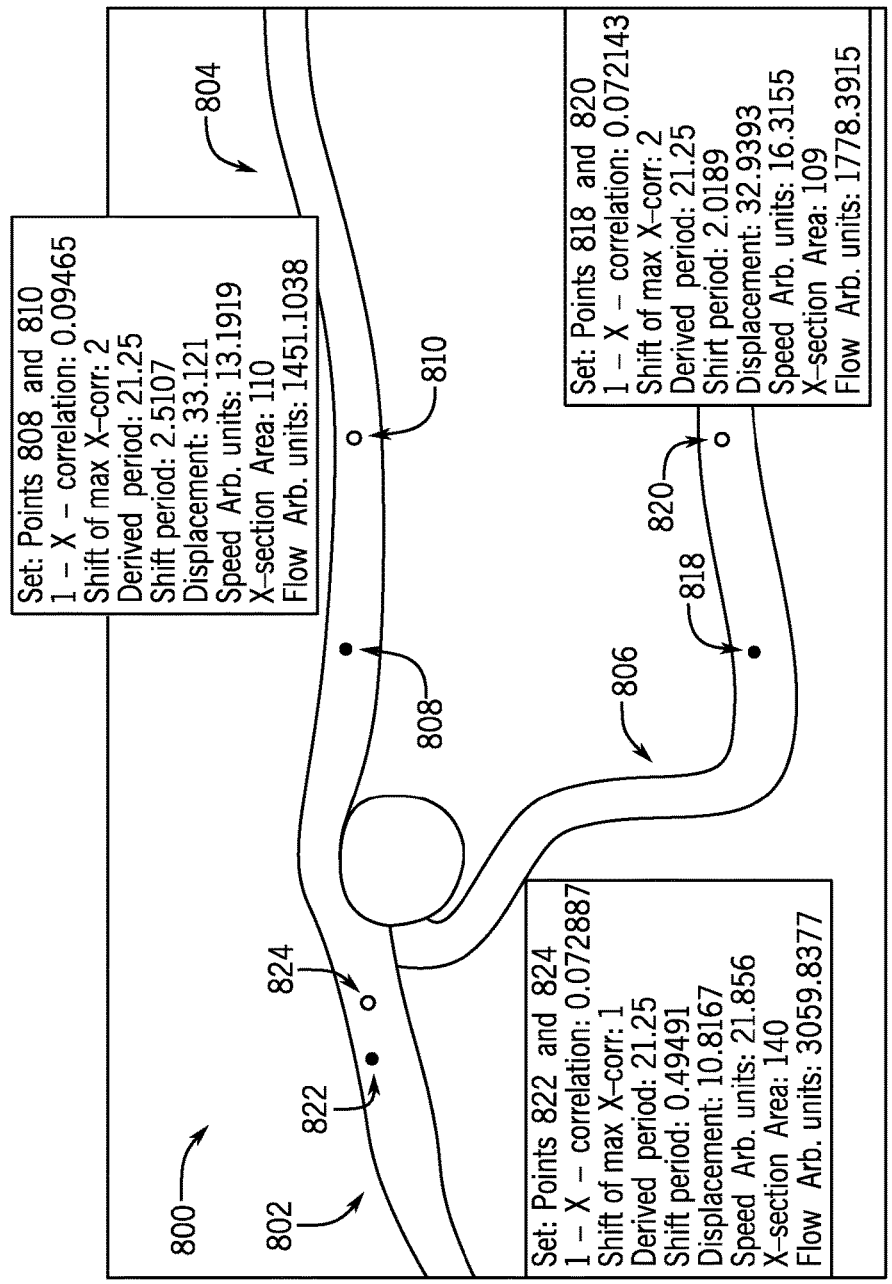
FIG. 8E is an image frame taken from a 4D DSA set showing the vessel of FIG. 8A having another two selected points along another branch.
FIG. 8F is a graph showing pulsatility waveforms associated with the selected points of FIG. 8E.
FIG. 8G is a graph of the power spectrum of the waveforms of FIG. 8F.
FIG. 8H is a graph of a cross correlation versus integer time frame shift for the waveforms illustrated in FIG. 8F.
FIG. 8 M is a an image frame taken from a 4D DSA set showing the vessel of FIGS. 8A, 8E, and 8I and the flow information associated with each branch.

Referring now to FIG. 8M, the analysis described above with respect to FIGS. 8A-8L has been combined with the respective derivations. As shown, the calculated flow in branch 802 is 3059.8337, which is approximately the sum of the flows in the other branches 804 (1451.1038) and 806 (1778.3915). As such, in this example, the systems and methods of the present disclosure have been demonstrated to provide verifiable results.

Thus, as described above, systems and methods are provided to exploit the pulsatile waveforms found in most vessels, as well as the time resolved three dimensional information regarding the vessel available from 4D DSA information, to provide 4D DSA images with dynamic physiological information, such as flow direction or velocity. The pulsatile waveforms can be reflective of the underlying pulsatile flow of blood through the vessel as driven by the subject's heart. Additionally or alternatively, the pulsatile waveforms may reflect an artificial pulsatile flow through the vessel, such as caused by a pulsed vascular injection to the subject.

The present invention has been described in terms of one or more preferred embodiments, and it should be appreciated that many equivalents, alternatives, variations, and modifications, aside from those expressly stated, are possible and within the scope of the invention.

What is claimed is:

1. A system for generating time resolved series of angiographic volume images having flow or velocity information integrated therewith, the system comprising:
an image processing system having a processor configured to:
receive angiographic volume data acquired from a subject having received a dose of a contrast agent using an imaging system;
process the angiographic volume data to generate angiographic volume images;
process the angiographic volume data to derive flow information associated with vessels in the angiographic volume images by:
determining a distance between two points along a vessel in the angiographic volume images;
determining a phase at each of the two points along the vessel in the angiographic volume images;
determining at least one of a flow direction or a velocity of flow within the vessel using the distance between the two points along the vessel and the phase at each of the two points along the vessel;
a display configured to display the angiographic volume images of the subject and the at least one of the flow direction or the velocity of flow within the vessel; and
wherein angiographic volume data includes x-ray projection data.

2. The system of claim 1 wherein the x-ray projection data includes four-dimensional (4D) digital subtraction angiography data.

3. The system of claim 1 wherein the display is configured to show the at least one of the flow direction or the velocity of flow within the vessel aligned with the vessel in the angiographic volume images.

4. The system of claim 1 wherein the image processing system is configured to determine one of a configuration or a centerline of a given vessel in a region of interest (ROI) in the angiographic volume images.

5. The system of claim 4 wherein the image processing system is configured to determine the distance between the two points along the vessel with respect to the centerline or a diameter of the vessel.

6. The system of claim 4 wherein the image processing system is further configured to perform one of a marching cube process and a rotating mask process to determine a flow direction within the given vessel in the ROI.

7. The system of claim 1 wherein the image processing system is configured to determine the phase at each of the two points along the vessel by analyzing a pulsatility at each of the two points along the vessel.

8. The system of claim 7 wherein the image processing system is configured to determine a temporal shift by examining at least one of a cross correlation or sum of square differences as a function of temporal shifts applied to a waveform of the pulsatility at one of the two points along the vessel.

9. The system of claim 7 wherein the image processing system is configured to perform a cross-correlation-versus-integer-time-frame-shift analysis and identify a minimum that gives a temporal shift, Δt, that, when combined with the distance between the two points along the vessel in the angiographic volume images, Δx, provides the velocity of flow between the two points along the vessel in the angiographic volume images.

10. A system for generating time resolved series of angiographic volume images having flow or velocity information integrated therewith, the system comprising:
an image processing system having a processor configured to:
receive angiographic volume data acquired from a subject having received a dose of a contrast agent using an imaging system;
process the angiographic volume data to generate angiographic volume images;
process the angiographic volume data to derive flow information associated with vessels in the angiographic volume images by:
determining a distance between two points along a vessel in the angiographic volume images;
determining a phase at each of the two points along the vessel in the angiographic volume images;
determining at least one of a flow direction or a velocity of flow within the vessel using the distance between the two points along the vessel and the phase at each of the two points along the vessel;
a display configured to display the angiographic volume images of the subject and the at least one of the flow direction or the velocity of flow within the vessel;
wherein angiographic volume data includes x-ray projection data;
wherein the image processing system is configured to determine the phase at each of the two points along the vessel by analyzing a pulsatility at each of the two points along the vessel; and
wherein the image processing system is configured to perform a Fourier analysis on a pulsatility waveform at each of the two points along the vessel to determine a peak associated with a characteristic pulsatile frequency of the pulsatility and determine the phase relative to the peak for pulsatility waveform at each of the two points along the vessel.

11. The system of claim 10 wherein the image processing system is configured to determine a temporal shift, Δt, given by:

$$\Delta t = (\phi_1 - \phi_2)\frac{1}{2\pi f};$$

where f is a characteristic pulsatile frequency of the pulsatility and $\phi_1$ and $\phi_2$ are phase relative to the peak for pulsatility waveform at each of the two points along the vessel.

12. The system of claim 11 wherein the image processing system is configured to determine the velocity pointing along the determined centerline in the direction of flow given by the sign of Δt and at a speed of Δx/Δt.

13. The system of claim 10 wherein the characteristic pulsatile frequency is determined using a sideband analysis in which a trial point in a power spectrum is compared with average sidebands.

14. A system for generating time resolved series of angiographic volume images having flow or velocity information integrated therewith, the system comprising:
an image processing system configured to:
receive angiographic volume data acquired from a subject having received a dose of a contrast agent using an imaging system;
process the angiographic volume data to generate angiographic volume images;
determine a distance, Δx, between two points along a vessel in the angiographic volume images separated by an absolute distance;
analyze respective waveform of pulsatility for each of the two points along a vessel in the angiographic volume images;
determine a point in a cross-correlation or sum-of-square differences between the respective waveform of pulsatility for each of the two points along a vessel to determine a time delay, Δt, corresponding to an estimate of a distance blood has traveled during the time delay that agrees with the distance Δx;
a display configured to provide the generate angiographic volume images correlated with the an indication of velocity between at least the two points along a vessel given by Δx/Δt.

15. The system of claim 14 wherein a sign of Δx/Δt indicates a direction of flow between at least the two points along a vessel.

* * * * *